United States Patent [19]
Gershman

[11] Patent Number: 5,432,834
[45] Date of Patent: Jul. 11, 1995

[54] WHOLE-BODY DUAL-ENERGY BONE DENSITOMETRY USING A NARROW ANGLE FAN BEAM TO COVER THE ENTIRE BODY IN SUCCESSIVE SCANS

[75] Inventor: Russell J. Gershman, Middleborough, Mass.

[73] Assignee: Hologic, Inc., Waltham, Mass.

[21] Appl. No.: 156,287

[22] Filed: Nov. 22, 1993

[51] Int. Cl.6 .............................................. G21K 5/10
[52] U.S. Cl. ...................................... 378/196; 378/55; 378/146
[58] Field of Search ................. 378/62, 145, 146, 193, 378/195, 196, 197, 198, 54, 55, 56

[56] References Cited

U.S. PATENT DOCUMENTS

| | | | |
|---|---|---|---|
| 4,811,373 | 3/1989 | Stein | 378/56 X |
| 5,132,995 | 7/1992 | Stein | 378/146 X |
| 5,177,776 | 1/1993 | Ohmori et al. | 378/146 X |
| 5,228,068 | 7/1993 | Mazess | 378/55 X |
| 5,287,546 | 2/1994 | Tesic et al. | 378/54 |
| 5,305,368 | 4/1994 | Bisek et al. | 378/196 X |

*Primary Examiner*—David P. Porta
*Attorney, Agent, or Firm*—Cooper & Dunham

[57] ABSTRACT

A dual energy bone densitometer scans the whole body of a patient in successive passes with a narrow fan beam of x-rays and, between passes, moves the patient table along multiple axes and rotates the C-arm about a rotation axis spaced from the focal spot. The coordinated multi-axes motion of the table and C-arm helps in piecing together the x-ray data from different passes and helps reduce the footprint of the instrument.

32 Claims, 7 Drawing Sheets

WHOLE-BODY DUAL-ENERGY BONE DENSITOMETRY USING A NARROW ANGLE FAN BEAM TO COVER THE ENTIRE BODY IN SUCCESSIVE SCANS

BACKGROUND OF THE INVENTION

This invention relates to x-ray analysis systems and methods.

X-rays or gamma-rays can be used to measure the density and distribution of bone in the human body in order to help health professionals assess and evaluate projected bone mineral density, which in turn can be used to monitor age-related bone loss that can be associated with diseases such as osteoporosis. Additionally or alternatively, similar procedures can be used to measure non-bone related body content such as body fat and muscle.

In general, in bone densitometry a patient is placed on a table while a radiation source irradiates the patient. An x-ray detector is positioned on the opposite side of the patient from the source to detect the radiation transmitted through the patient. The x-ray source and detector are usually mechanically linked by a structure such as a C-arm to ensure alignment of source and detector. Both x-ray tubes and isotopes have been used as a source of the radiation. In each case, the radiation from the source is collimated to a specific beam shape prior to reaching the patient to thereby restrict the field of x-ray or gamma radiation to the predetermined region of the patient opposite which are located the detectors. In the case of using x-rays, various beam shapes have been used in practice including fan beam, pencil beam and cone or pyramid beam shapes.

The shape of the beam and the shape of the detector system correspond. The detector in a fan beam system typically is a linear array of detectors. Some examples of the actual detectors which make up the array are the relatively low cost silicon photo diodes coupled with a scintillation material and the relatively high cost photo multiplier tubes coupled with scintillation material. In both cases, the cost of the detector system and associated electronics increases substantially with increasing numbers of detectors.

By means of mechanically moving the source/detector system relative to the patient, the fan beam of x-rays can be scanned in a direction normal to the plane defined by the boundaries of the fan beam angle to produce a rectangular analysis area. The width of this rectangular area is defined by the width of the fan beam when it passes through the patient. Of course, it is desirable that the scanned area include the desired region of analysis.

Typical regions of analysis in bone densitometry include the spine, hip and wrist, scanned individually. They can be covered individually within a reasonable time by a fan beam that has a relatively narrow angle in a single pass or, alternatively, by a pencil beam scanning a raster pattern. Another analysis region is termed "oblique hip" in which the hip is viewed at an angle relative to the horizontal and vertical directions. This can be desirable for optimizing the projection angle through the femoral neck. However, current techniques typically require patient leg positioning which can result in imprecise measurements on repeated scans of the same patent.

Another analysis region is referred to as "whole body" in which the entire patient body is scanned and analyzed for bone density and possibly also for "body composition" or the percentages of fat and muscle in the body. Known whole body procedures have utilized pencil beam scans of the patient, using a relatively narrow beam of radiation and a single detector scanning the whole body in a raster scan. However, such a scan takes a considerable length of time. If the whole body is to be scanned in a single pass with a fan beam of radiation, the fan angle would have to be considerably greater than that required for other typical analysis such as hip, spine or wrist analysis. This implies that the detector array must also be substantially wider than an array for wrist, hip or spine analysis if whole body analysis is to proceed by using only pass of the beam over the patient. Alternatively, one could utilize multiple longitudinal passes of the patient body using a smaller and less expensive detector array but the data from the multiple passes would need to be merged without artifacts especially at the boundaries between passes.

Known system of this type are manufactured by the assignee hereof under the tradenames QDR-2000, QDR-1500, QDR-1000plus, and QDR-1000. The following commonly owned U.S. Pat. Nos. pertain to such systems and are hereby incorporated by reference herein: 4,811,373, 4,947,414, 4,953,189, 5,040,199, 5,044,002; 5,054,048, 5,067,144, 5,070,519, 5,132,995 and 5,148,455; and 4,986,273 and 5,165,410 (each assigned on its face to Medical & Scientific Enterprises, Inc. but now commonly owned). Other bone densitometry systems are believed to be offered by the Lunar Corporation of Madison, Wis. (see, e.g., the system which is believed to be offered under the tradename Expert and U.S. Pat. No. 5,228,068, neither of which is admitted to be prior art against this invention).

SUMMARY OF THE INVENTION

According to one important aspect of the invention, an x-ray analysis system comprises an x-ray source which generates and projects at least one x-ray beam along a plane transverse to a patient's long axis, and detector array arranged on the opposite side of the patient to detect x-rays so as to produce signals corresponding to the amount of x-rays transmitted through the patient. The detector array together with and in fixed relation to the x-ray source is movable relative to the patient in a scanning direction normal to the beam plane through a multiplicity of scan line positions called a "pass" or a j"scan." The detector outputs from multiple passes or scans for different areas of the patient can be combined to yield one equivalent pass or scan of a larger area for subsequent analysis.

Preferred embodiments of this aspect of the invention include one or more of the following features: The x-ray source comprises an x-ray tube and a slit collimator that produces a fan beam. The detector array includes a linear array of evenly spaced discrete detectors. The x-ray source and detector array are translatable in a direction normal to the detector array to produce a movement in the scanning direction. In addition, the x-ray source and detector array are rotatable to fixed angular positions to produce scanning beams at other angles which cover other areas of the patient or to cover the same general area at different angles. The patient is on a table which is movable in at least the vertical direction and one horizontal direction to allow the focal spot of the x-ray tube to remain in a fixed vertical distance from the table. This makes it possible to combine the detector output from scans at different angles into an accurate composite x-ray image because in accordance with one aspect of the invention, the fan beams for each pass or scan can all emanate from a common focal spot location, i.e., the focal spot for each fan beam can be exactly in the same location relative to the patient. Therefore, the projection through bone and other tissue seen at adjacent beam boundaries can be sufficiently similar to allow for an image seamed from multiple pass fan beams to be the same or equivalent to an image that could have been derived from a single pass with a fan beam wide enough to encompass the entire width of the patient.

An exemplary and non-limiting method in accordance with the inventions comprises placing a patient on a table movable in a vertical direction and in a direction along the width of the patient, irradiating the patient with a fan beam of x-rays subtending an angle that includes substantially less than the body width of the patient; receiving x-rays from the source within the angle subtended by the fan beam after passage thereof through the patient at a number of radiation detecting position arrayed within said angle; scanning the fan beam and the detector along the length of the patient in successive scans; selectively moving the table both along the width of the patient and vertically between successive scans to thereby scan the patient from different angles while maintaining a selected vertical distance between an origin of the fan beam and the table; and integrating the detector outputs from the successive scans into a single whole-body image. In addition to this process, or instead of this process, the vertical distance between the origin of the x-rays and the table, and the angle of the beam to the patient, can be changed and the beam can be scanned relative to the patient to obtain detector outputs for a lateral view and/or an oblique hip view without moving the patient relative to the table.

BRIEF DESCRIPTION OF THE DRAWINGS

A more complete understanding of the invention may be obtained from the following description when taken in conjunction with the drawings, in which.

DESCRIPTION OF A PREFERRED EMBODIMENT

Figure 1:
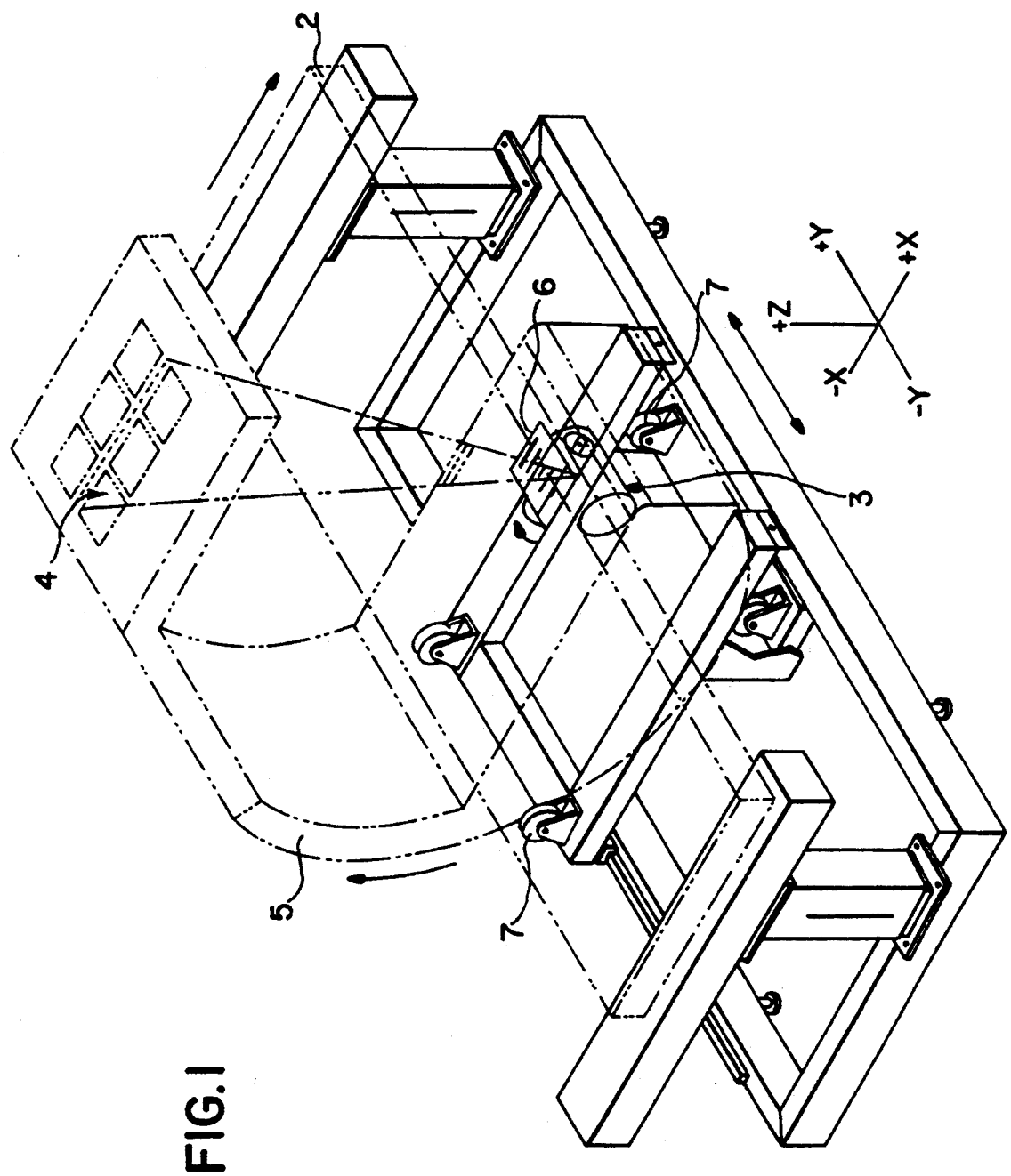
FIG. 1 is a diagrammatic representation of an embodiment of the invention.

Referring to FIGS. 1, 2A, 2B and 2C, a patient 1 lies horizontally during scanning on a table 2. X-ray radiation produced by an x-ray source 3 located beneath table 2 is transmitted through patient 1 to a detector 4 having an array of detector positions and located above patient 1. Both x-ray source 3 and detector 4 are supported on a rigid arm 5 which maintains a selected source-to-detector distance and alignment. In this example of the invention, x-ray source 3 has a stationary anode. Adjacent x-ray source 3 is a slit collimator 6 made of a material an x-ray opaque material such as lead or tungsten of sufficient thickness to substantially block x-rays from source 3. One or more selectable slits have been machined into collimator 6 to allow passage of the x-rays therethrough. The preferred embodiment includes a 1 mm wide collimator slit. The x-ray radiation from the x-ray source 3 passes through the slit in the collimator 6 and forms a fan shaped beam of x-rays 3a. The angle subtended by beam 3a and the distance between its origin at the focal spot of the x-ray tube and patient 1 are selected such that beam 3a would not cover the entire cross-section of a typical adult patient at any one time but would cover only a selected portion of the width. In the preferred embodiment, fan beam 3a has a maximum fan angle of 22 degrees, whereas a fan angle of 65 degrees may be required to completely cover patient 1 for whole body analysis. Of course, x-ray beam 3a not only has width (along the X-axis illustrated in the Figures) but also has a thickness along the Y-axis that is defined by the width of the slit in collimator 6 and its distance from the origin of beam 3a. A scan line is defined by the area of the patient irradiated at any one time, i.e. the width and thickness of the x-ray beam over which data is collected at one point in time. A complete pass or scan consists of a set of adjacent scan lines obtained over a period of time such that the entire region of interest has been measured.

Opposite x-ray source 3 is detector 4 which in this embodiment comprises approximately 200 detector elements arranged in a linear configuration along the XZ plane which is about 16" long and is about 42" from the origin of beam 3a (42" source-to-detector spacing) and subtends a 22 degree fan angle. The detector elements making up detector 4 are fixed with respect to x-ray source 3. However, both x-ray source 3 and detector 4 can move with respect to patient 1 and table 2. One motion translates fan beam 3a along the patient axis defined by the spine, i.e., in the Y-direction. Another motion rotates beam 3a around the patient. The center of rotation is at a point C (see FIG. 5A) determined by the support arm 5 and the method of rotation employed. In this embodiment, the detectors and x-ray source are mounted to C-arm 5 which rotates on a set of rollers 7. Thus, the center of rotation is determined by the outer radius R of the C-arm, and is not at the origin (focal spot) of beam 3a.

Patient 1 lies on a table 2, for example in the supine position. Table 2 can move horizontally along the X-axis as well as vertically along the Z-axis. These motions can be carried out by using a toothed-belt driven by a stepping motor or a DC servo motor, although other implementations such as stepper-motor driven lead-screws can also be employed. To perform a scan, a series of scan lines of data must be acquired. To do this, C-arm 5 carrying the x-ray source 3 and detector 4 is moved along the Y-axis along the length of patient 1. This motion moves detector 4 and x-ray source 3 to form a succession of spatially overlapping scan lines adding up to a scanned rectangular area. The signals produced by the detectors in response to x-rays impinging thereon at successive scan lines are digitized by an analog to digital (A/D) converter and are stored, for example on disk. A computer processes the signals from the A/D converter into density representations and images using the principles disclosed in the prior art discussed in the background section of this disclosure.

Figure 2C:
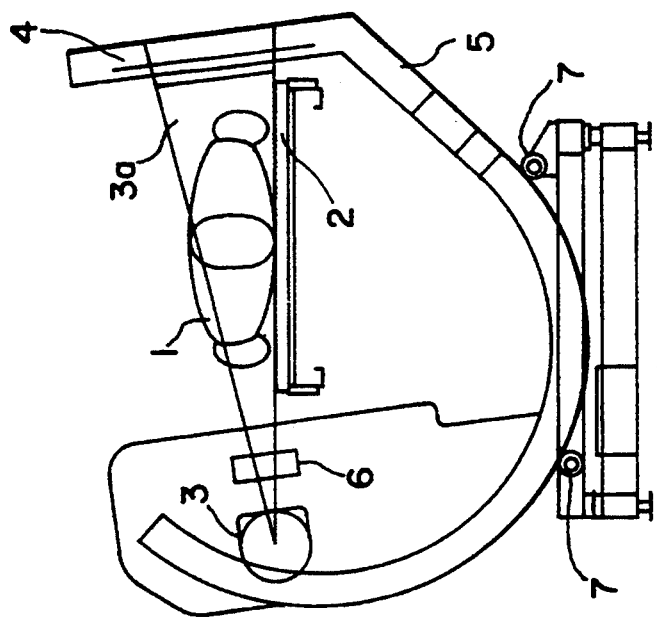
FIG. 2C is an end-on view for a lateral spine measurement.
Figure 2B:
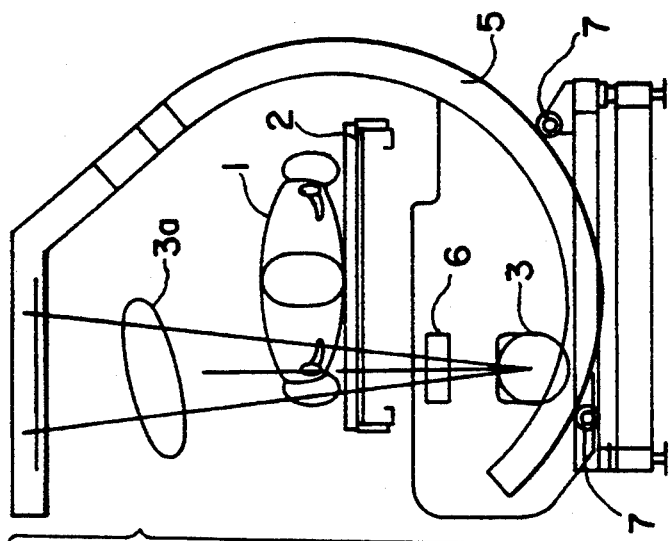
FIG. 2B is an end-on view for a hip measurement.
Figure 2A:
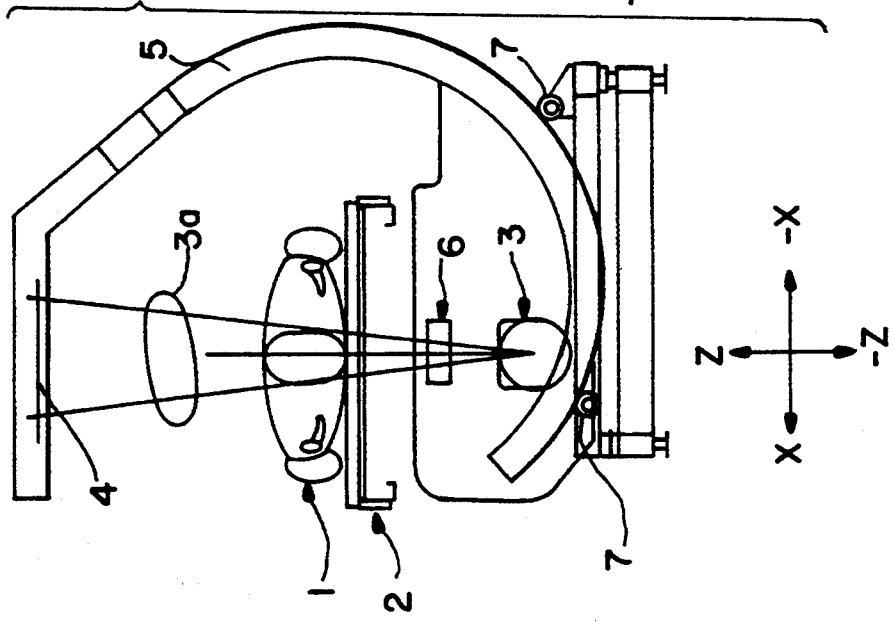
FIG. 2A is an end-on view of a patient table and a C-arm of the embodiment of FIG. 1, in the position to perform a PA (posterior-anterior) spine measurement.

For body structures of interest such as the spine, hip and wrist, only a single pass of fan beam 3a along the Y-axis is required because typically the area of interest in the patient's body is covered by fan beam 3a as shown in FIG. 2A for the Posteroanterior (PA) spine and in FIG. 2B for the hip. Indeed, a fan beam of only 14 degrees can be sufficient for the geometry of this embodiment to fully illuminate these body areas with x-rays. FIG. 2C shows the positioning for a lateral scan of the spine in which the view is orthogonal to the standard PA spine view. To attain this position, a series of movements of C-arm 5 and table 2 are required to ensure that the table and C-arm clear each other. In this embodiment, table 2 is moved along the X-axis and the Z-axis appropriately while C-arm 5 is rotated about an Y-axis passing through point C until the desired lateral position is reached.

Figure 3A:
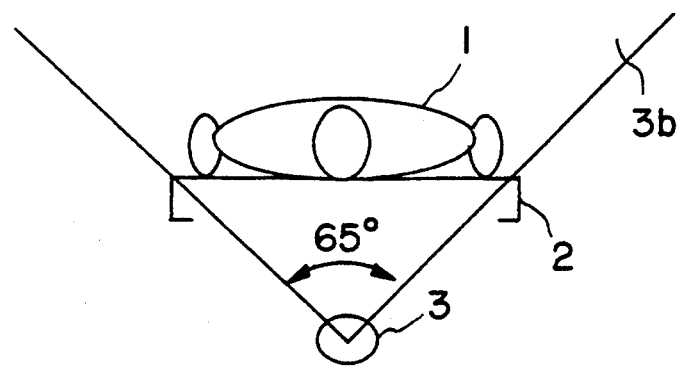
FIGS. 3A, 3B and 3C are representations of x-ray fan beam coverage of a patient for whole body measurement illustrating the use of a wide fan beam made up or three passes or scans and involving rotating an x-ray tube around the focal spot from which it emits x-rays.
Figure 3B:
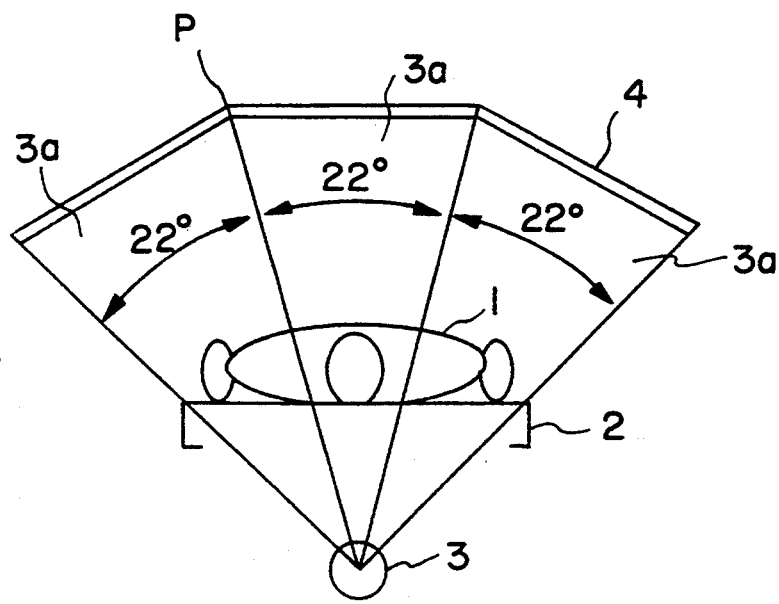

Whole body analysis requires that the entire body be illuminated with x-rays. Referring to FIG. 3A, a fan beam 3b of approximately 65 degrees can be suitable for completely illuminating the entire cross-section of patient 1. As illustrated in FIG. 3B, this fan beam can be simulated by utilizing multiple passes from a smaller, 22 degree fan beam 3a as long as all of the fan beams emanate from the same focal spot location to maintain the focal spot to patient body relationship. With a fan beam 3a of 22 degrees and the nominal dimensions of the system in this embodiment, three passes along the Y-axis can be made to cover the entire patient 1. Thus, data from passes 1, 2 and 3 from the smaller fan beam 3a can be added together using a computer to provide data that is substantially equivalent to data that would have been obtained if one large fan beam 3b had been used. To provide the smaller fan beams implies rotation of fan beam 3a with the focal spot thereof as the center of rotation. With fan beam 3a in a vertical orientation as in the middle position of fan 3a in FIG. 3B, fan beam 3a for pass 1 is rotated 21.5 degrees from the vertical while fan beam 3a for pass 3 is rotated −21.5 degrees from the vertical. The data from the 0.5 degrees of overlap is blended, e.g., by progressively using more of the data from the next pass as one moves in angle toward the next pass, using for example principle known in second generation CT technology.

Figure 3C:
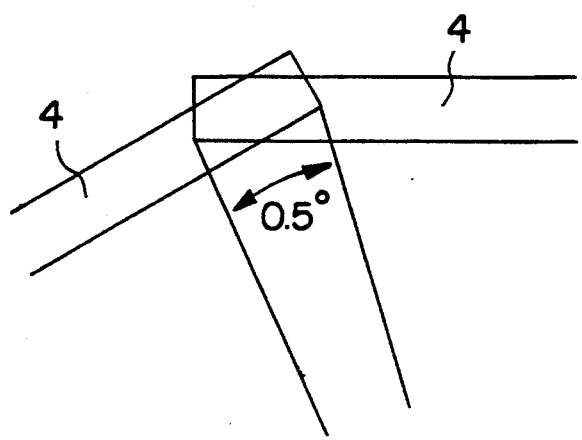

FIG. 3C shows an enlargement of the area designated P in FIG. 3B, where beams 3a for passes 1 and 2 overlap spatially. Fan beam 3a is slightly wider than the required 21.5 degrees so that there is an overlap of 0.5 degrees between the two passes. The overlapping areas imply that at least two different elements of detector 4 have measured the x-rays attenuated through the same body area.

If rotation of beam 3a around its focal spot is possible, implementation of the multiple passes is relatively easy because the only required motion between passes is rotation. However, in the preferred embodiment, the center of rotation C does not coincide with the focal spot. To overcome this, in accordance with the invention the focal spot is made the effective center of rotation through motion of table 2.

Figure 4C:
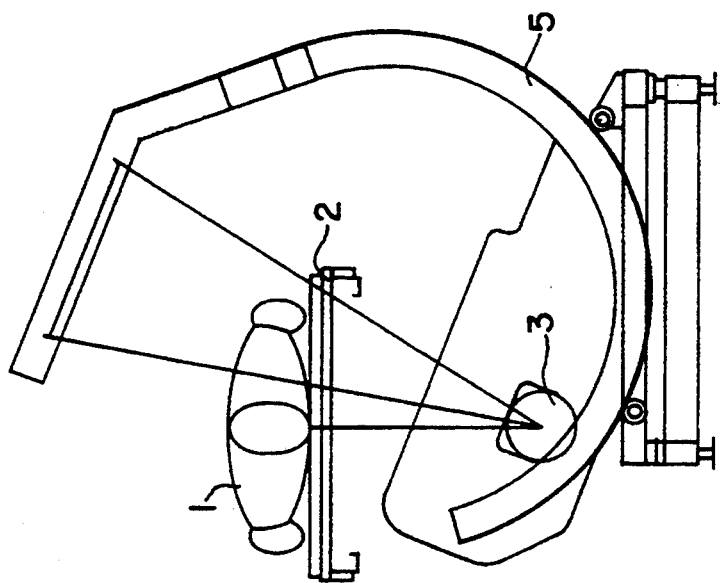
FIG. 4A, 4B and 4C are end-on views of a preferred embodiment of the invention for whole-body measurement showing the C-arm/patient table positioning for the three measurement passes or scans.
Figure 4B:
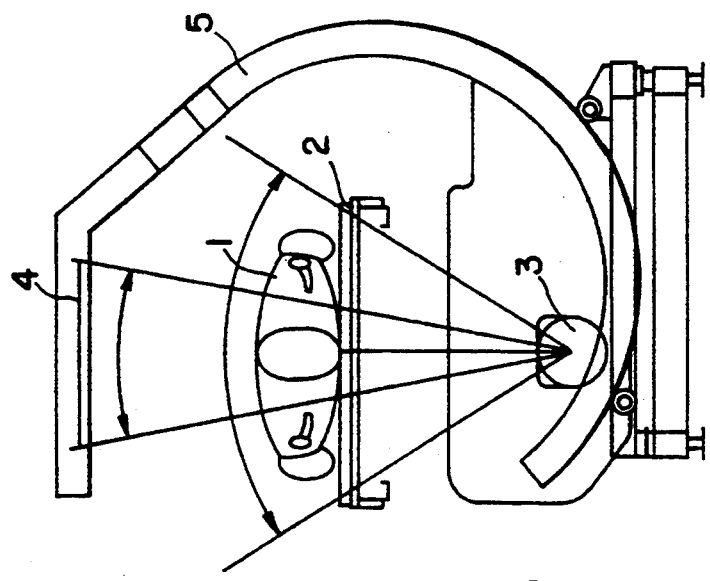
Figure 4A:
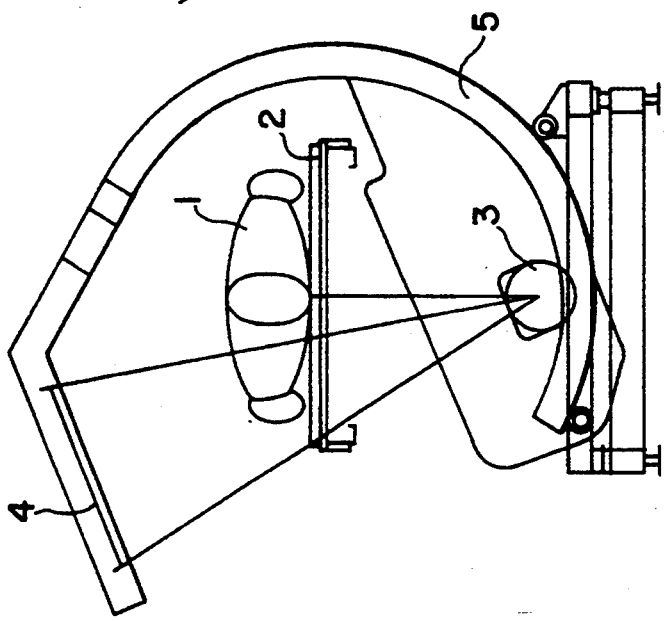

Referring to FIGS. 4A, 4B and 4C, the three views depict the relative position of table 2 and C-arm 5 for the three passes in the preferred embodiment. Collimator 6 is not shown in these views. Each position maintains constant the spacing between the focal spot of beam 3a and table 2 as well as the location of a vertical intercept from the focal spot to table 2.

Figure 5A:
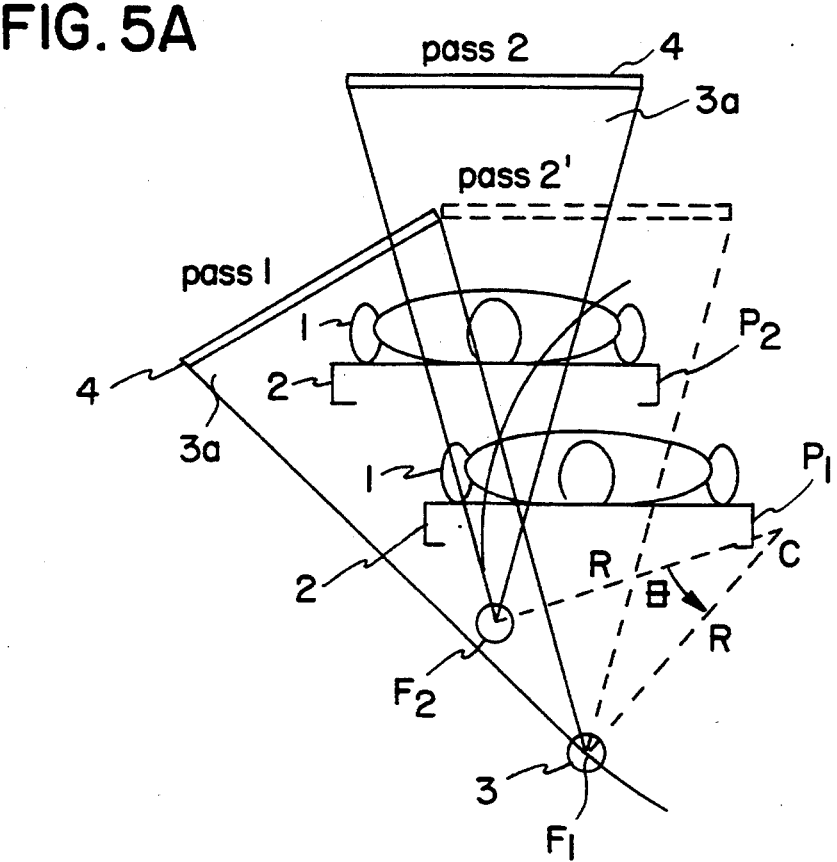
FIG. 5A and 5B depict the relationship between the x-ray source and patient table position for two measurement passes in accordance with an embodiment of the invention.
Figure 5B:
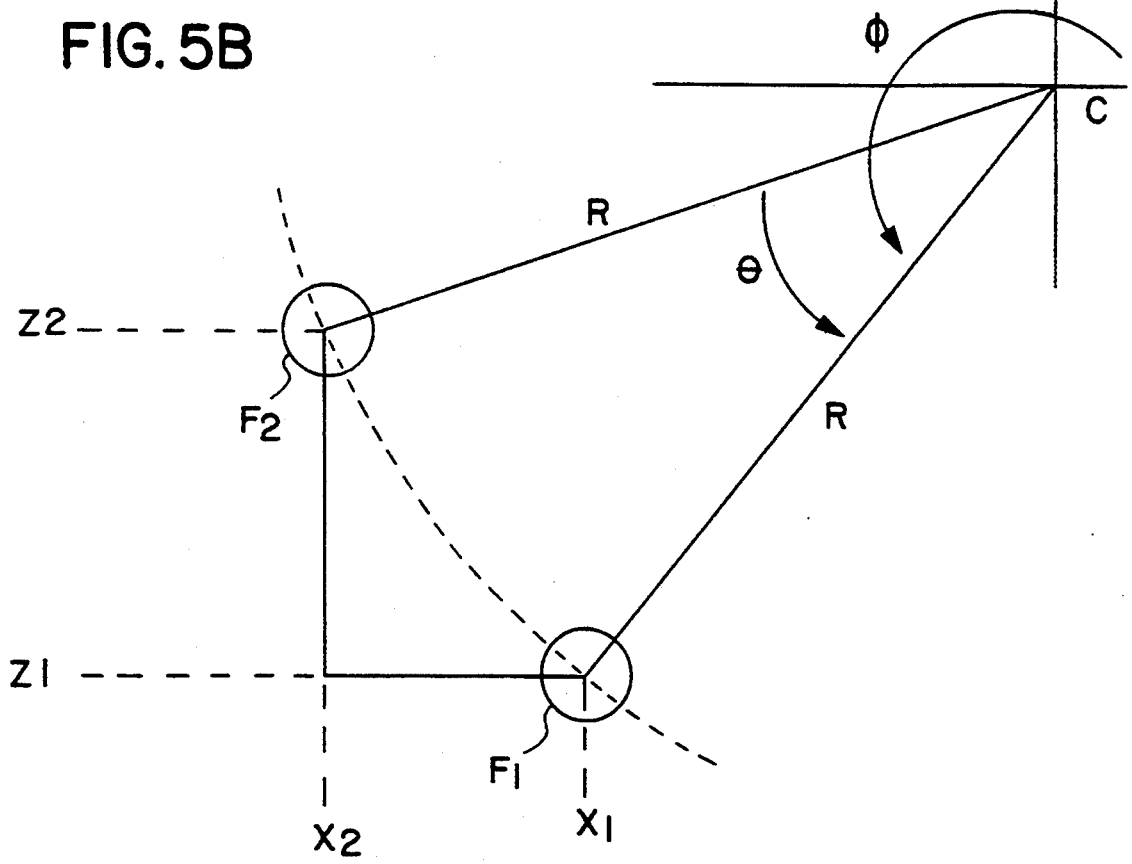

In FIG. 5A the geometry of pass 1 in relation to pass 2 is detailed. In pass 1, patient 1 lies supine on patient table 2 at position P1 with the focal spot of x-ray source 3 located at F1. In this position, only the left side of patient 1 is illuminated with x-rays within fan beam 3a. If C-arm 5 could now be rotated about the focal spot, the conditions of pass 2' would be achieved in which the central part of the patient would be illuminated. However, the focal spot rotates about the center of rotation of C-arm 5 located at C with a radius R. A rotation through an angle of $-\theta$ about a pivot axis at point C attains the positioning of pass 2 in which the focal spot is located at F2. To maintain the focal spot of beam 3a as the effective center of rotation, patient table 2 moves to position P2 (without moving patient 1 relative to table 2) in which the spatial relations between F1 and P1 are identical to the spatial relations between F2 and P2, i.e., a vertical drawn from the focal spot intersects patient table 2 at the same point and extends over the same distance. To attain position P2 requires two motions of table 2, one over a distance DX along the X-axis and another over a distance DZ along the Z-axis. These two motions can be consecutive or concurrent. These distances DX and DZ correspond to the differences in X and Z coordinates for focal spot positions F1 and F2. Referring to FIG. 5B, where the terms are graphically defined, the distances DX and DZ are given by the relationships:

$$DX = (X2 - X1) = R[\cos \phi(\cos \theta - 1) + \sin \phi \sin \theta]$$

$$DZ = (Z2 - Z1) = R[\sin \phi(\cos \theta - 1) - \cos \phi \sin \theta]$$

Patient table 2 is translated along the Z-axis over a distance DX and along the Z-axis over a distance DZ, where $\phi$ is the angle that F1 makes with the center of rotation C as the origin and $\theta$ is the angle of rotation between F1 and F2 which in the preferred embodiment is about −21.5 degrees, with the negative angle denoting a clockwise rotation around C between passes 1 and 2. Similarly, for pass 3, the focal spot is translated by DX and DZ with $\theta = -43$ degrees.

Although the preferred embodiment uses translations of table 2 along the X-axis and Z-axis to maintain the table/focal spot relationship, other embodiments are possible within the scope of the disclosed inventions without loss of generality. For instance, C-arm 5 can be made movable along the X-axis and the Z-axis while table 2 remains stationary, or table 2 and C-arm 5 can share the translations, i.e., C-arm 5 can move along the X-axis (or the Z-axis) while table 2 moves along the Z-axis (or along the X-axis).

Figure 6:
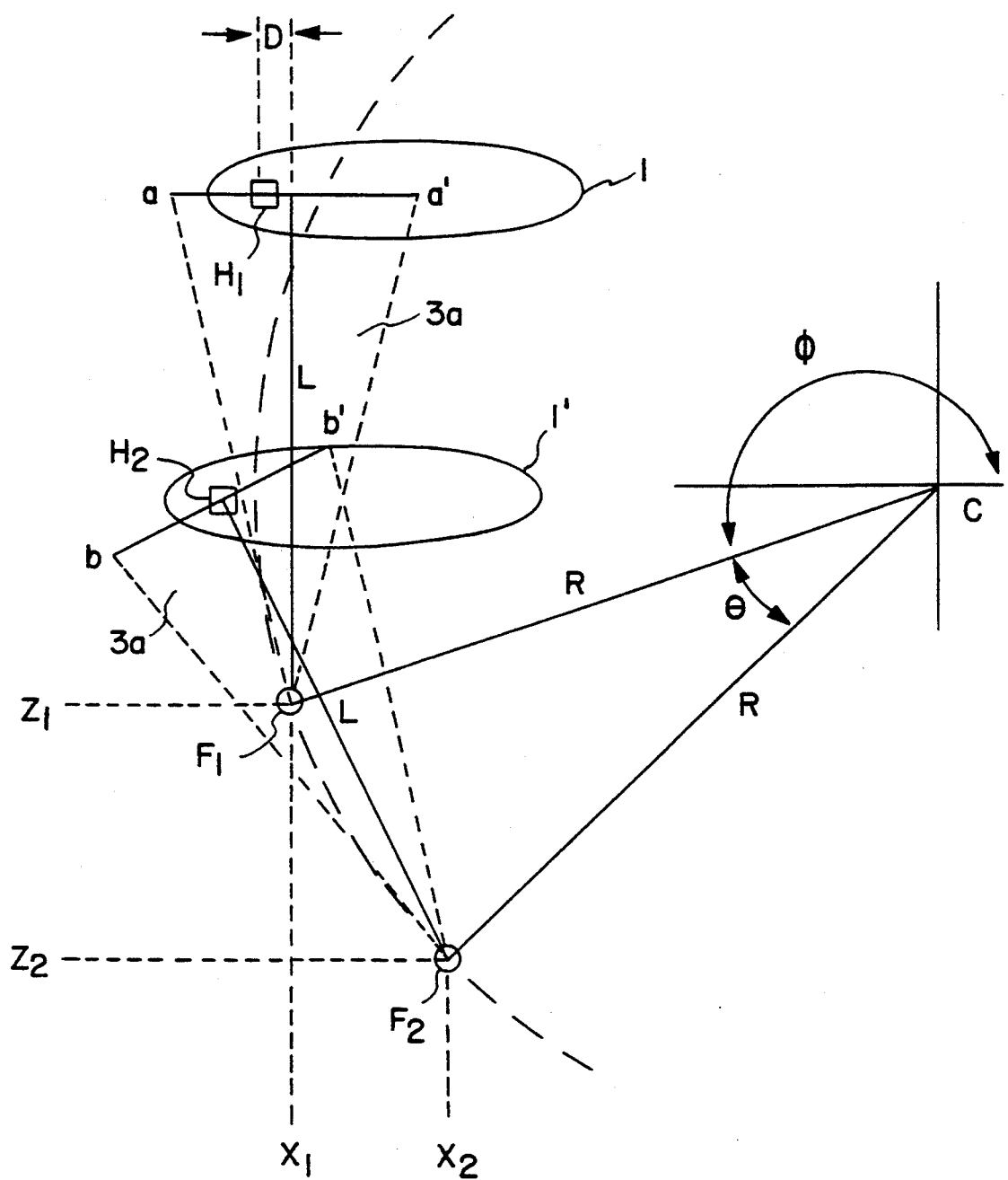
FIG. 6 depicts the relationship between the x-ray source and the patient table for an oblique hip measurement in which the x-ray beam is angled relative to the patient in a manner similar to that illustrated in FIGS. 4A and 4B.

As illustrated in FIG. 6, an additional analysis called the "oblique hip" can be performed in accordance with the invention by suitably rotating C-arm 5 and translating patient table 2 along the X-axis and the Z-axis. The actual position can be determined beforehand by performing a "scout" scan which is usually a high speed, low dosage scan for the AP hip. In FIG. 6, F1 is the location of the focal spot of beam 3a, and line a–a' represents the field of radiation in patient 1, at a distance L from the focal spot of beam 3a. For convenience and clarity, patient table 2 is not shown in FIG. 6, but its position can be seen in FIG. 4a. A hip designated H1 is offset from the central ray of beam 3a by a distance D which can be quantitatively determined from the scout scan. Upon rotation of C-arm 5 through an angle $\theta$ (or 23 degrees in the preferred embodiment) the focal spot is now at F2. Table 2 is translated along the X-axis and the Z-axis while patient 1 remains stationary on table 2 so that the patient's hip is at position H2 which is now located in the central ray F2-H2 of the radiation field b–b' in patient 1. In this geometry, the X and Z translations, DX and DZ, of table 2 made to place the hip at H2 are given by the relationships:

$$DX = R \cos \phi [\cos \theta - 1] - \sin \phi [R \sin \theta - L] + D$$

$$DZ = [R \sin \phi + L][\cos \theta - 1] + R \cos \phi \sin \theta$$

where R is the distance of the focal spot F1 from the center of rotation C of the focal spot of beam 3a, and $\phi$ is the angle of the focal spot F1 with respect to the center of rotation C. The distance L from the focal spot to the hip is estimated as the sum of the known distances from F1 to the table plus the estimated distance from the table to the field a–a'.

Figure 7:
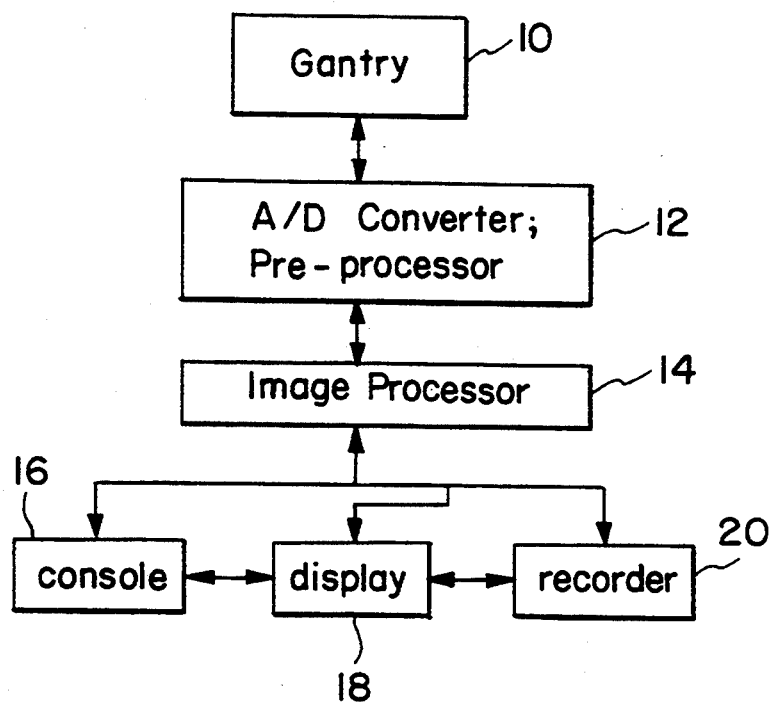
FIG. 7 is a block diagram illustrating an embodiment of the invention.

FIG. 7 illustrates an embodiment in accordance with the invention in block diagram form. Gantry 10 includes the structure illustrated in FIG. 1 as well as a suitable power supply for the x-ray tube and the motors needed to move table 2 and C-arm 5 and to operate collimator 6 in a manner similar to that in said QDR-2000 system. Detector 4 supplies x-ray measurements to A/D convertor and preliminary processor 12 which carries out processing similar to that carried out in said QDR-2000 system. The output of element 12 is supplied to a processor 14 which performs various calculations and forms an image in a manner similar to that used in said QDR-2000 system and, additionally, blends the data from successive scans in a manner similar to that used in second generation CT technology to form whole-body images. Data and images from processor 14 are supplied to a console 16, display 18 and a recording device 20 for purposes and in a manner similar to those in said QDR-2000 system. Two-way arrows connect the elements of FIG. 8 to illustrate the fact that two-way communication can take place therebetween. Conventional elements have been omitted from the Figures and from this description for the sake of conciseness.

While a preferred embodiment of the invention has been described in detail, it should be understood that changes and variations will be apparent to those skilled in the art which are within the scope of the invention recited in the appended claims.

I claim:

1. A whole body x-ray bone densitometry system comprising:

a table extending parallel to a Y-axis of an XYZ coordinate system for supporting a patient at a patient position;

an x-ray source for emitting a narrow angle fan beam of x-rays to irradiate at any one time a scan line which is transverse to the Y-axis and is substantially shorter than the width of a body cross-section of a typical adult patient occupying the patient position;

an x-ray detector aligned with said source along a source-detector axis which is transverse to the Y-axis, for receiving x-rays from the source within the angle of said fan beam after passage thereof through the patient position, said detector comprising a number of detecting elements arranged along a direction transverse to the Y-axis and to the source-detector axis;

a source-detector support on which the source and detector are mounted at opposite sides of the patient position; and a scanning mechanism moving at least one of the patient table and the source-detector support relative to the other to scan the patient position with said narrow angle fan beam in successive scans parallel to the Y-axis in which the source-detector axis is at different angles relative to the patient position as between different ones of said successive scans but in each of said successive scans an origin of the fan beam in the source is at the same vertical distance from the patient table.

2. A system as in claim 1 in which said scanning mechanism comprises a table moving mechanism selectively moving the table parallel to the X-axis between said successive scans.

3. A system as in claim 2 in which said table moving mechanism comprises a mechanism selectively moving the table parallel to the Z-axis between said successive scans.

4. A system as in claim 3 in which said scanning mechanism comprises a rotating mechanism selectively rotating the source-detector support about a rotation axis parallel to the Y-axis between said successive scans.

5. A system as in claim 4 in which said scanning mechanism comprises a mechanism moving the table between at least two of said successive scans through a motion having a component parallel to the X-axis over a distance DX and a component parallel to the Z-axis over a distance DZ, where the distances DX and DZ are according to the expressions:

$$DX = (X_2 - X_1) = R[\cos \phi (\cos \theta - 1) + \sin \phi \sin \theta]$$

$$DZ = (Z_2 - Z_1) = R[\sin \phi (\cos \theta - 1) - \cos \phi \sin \theta]$$

where:

$X_1$ and $X_2$ are the positions of an origin of the fan shaped beam along the X-axis before and after the table motion, $Z_1$ and $Z_2$ are the positions of the origin along the Z-axis before and after the table motion, $\theta$ is the negative of the angle through which the source-detector axis pivots between the at least two successive scans, $\phi$ is the angle that the origin makes with the rotation axis at the end of the rotating motion of the source-detector support, and R is the distance between the origin and the rotation axis.

6. A system as in claim 5 in which said angle $\theta$ is about $-21.5$ degrees, with the negative angle denoting a clockwise rotation of the support about the rotation axis.

7. A system as in claim 6 in which the angle subsumed by said fan beam is about 22 degrees, and the fan beam positions between two of said successive scans overlap by about 0.5 degrees.

8. A system comprising:
a table for supporting a patient at a patient position, said table having a length and a left side and a right side which are spaced from each other in a direction transverse to the length of the table, said table being selectively movable at least left-right and up-down;
an x-ray source for emitting a fan beam of x-rays;
an x-ray detector receiving x-rays from the source within an angle subtended by said fan beam after passage thereof through the patient position, said detector comprising a number of detecting elements aligned with respective angular positions in the fan beam and arranged along a direction transverse to the length of said table;
a source-detector support supporting the source and detector at opposite sides of the patient position; and
a scanning mechanism selectively moving the source-detector support along the length of the table and selectively rotating the source-detector support around the table and selectively moving the table both left-right and up-down to scan the patient position with said fan beam in successive scans along the length of the table in which the source-detector support is at different angles relative to the table as between different ones of said successive scans but the up-down distance between an origin of the fan beam in the source and the table is the same for each of said successive scans.

9. A system as in claim 8 in which the scanning mechanism comprises a table moving mechanism which between said successive scans moves the table left-right and up-down and rotates the source detector support about a rotation axis that does not pass through the origin of the fan beam.

10. A system as in claim 9 in which said fan beam at said patient position is narrower than the width of a typical adult patient who is in the supine position on the table.

11. A system as in claim 10 in which said beam irradiates overlapping portions of said patient position in said successive scans.

12. A system as in claim 8 in which said scanning mechanism comprises a mechanism carrying out said successive scans for an anterior-posterior view of the patient position and selectively changing the up-down distance between said origin and the table and scanning the beam relative to the patient position for a lateral view without moving the patient relative to the table.

13. A system as in claim 12 in which said scanning mechanism additionally comprises a mechanism for changing the up-down distance between the origin and the table and scanning the patient with the fan beam for a hip view without moving the patient relative to the table.

14. A system as in claim 8 in which said scanning mechanism comprises a mechanism carrying out said successive scans for an anterior-posterior view and selectively changing the up-down distance between said origin and the table and scanning the beam relative to the patient position for a lateral view and a hip view without moving the patient relative to the table.

15. A method comprising:
placing a patient on a table;
irradiating the patient with a fan beam of x-rays subtending an angle that includes substantially less than the body width of the patient;
receiving x-rays from the source within the angle subtended by the fan beam after passage thereof through the patient at a number of radiation detecting positions aligned with angular positions within said angle;
scanning the fan beam and the detector along the length of the patient in successive scans and selectively moving at least one of the table and the fan beam along each of two orthogonal axis transverse to the length of the patient between said successive scans to scan the patient from different angles while maintaining a selected vertical distance between an origin of the fan beam and the table.

16. A method as in claim 15 in which the fan beam in said successive scans irradiates overlapping portions of the patient to generate detector measurements for an anterior-posterior view of the patient, and additionally comprising the step of changing the vertical distance between the origin and the table and scanning the beam relative to the patient to obtain a lateral view without moving the patient relative to the table.

17. A method as in claim 16 further comprising changing the vertical distance between the origin and the table and scanning the beam relative to the patient to obtain a hip view without moving the patient relative to the table.

18. A method as in claim 15 further comprising changing the vertical distance between the origin and the table and scanning the beam relative to the patient to obtain a hip view without moving the patient relative to the table.

19. A method comprising:
supporting a patient with the length thereof being along the Y-axis of an X,Y,Z orthogonal set of axes;
emitting a fan beam of x-rays from an origin to irradiate at any one time less than the entire width of the patient;
receiving x-rays from the source within an angle subtended by the fan beam after passage thereof through the patient at a number of individual detecting positions arranged along a plane normal to the Y-axis;
moving the fan beam and the detector concomitantly to scan the patient in successive scans which are along the Y-axis but in which the fan beam is at different angles to the patient, rotating the fan beam about a rotation axis parallel to the Y-axis between said successive scans, and moving the table along the X-axis and the Z-axis to maintain a selected vertical distance between the origin and the table to obtain detector outputs for an anterior-posterior view of the entire width of the patient while maintaining the patient's position relative to the table.

20. A method as in claim 19 further comprising selectively changing the vertical distance between the origin and the table and the angle of the beam to the patient and scanning the beam relative to the patient to obtain detector outputs for a lateral view without moving the patient relative to the table.

21. A method as in claim 20 further comprising selectively changing the vertical distance between the origin and the table and the angle of the beam to the patient and scanning the beam relative to the patient to obtain detector outputs for a hip view without moving the patient relative to the table.

22. A method as in claim 19 further comprising selectively changing the vertical distance between the origin and the table and the angle of the beam to the patient and scanning the beam relative to the patient to obtain detector outputs for a lateral view and a hip view without moving the patient relative to the table.

23. A method as in claim 19 further comprising processing detector outputs to form and display x-ray images of the patient.

24. A whole body x-ray bone densitometry method comprising:

supporting a patient on a table at a patient position, with the length of the patient being parallel to the Y-axis of an orthogonal X, Y, Z coordinate system and with the width of the patient being parallel to the X-axis;

emitting a fan beam of x-rays from an origin in a source at one side of the patient position to irradiate at any one time a scan line which is perpendicular to the Y-axis and has a length at the patient position which is less than the width of a body cross-section of a typical adult patient who is at the patient position;

receiving x-rays from the source, within the angle of said fan beam, after passage of the x-rays through the patient position, at an x-ray detector which comprises a number of x-ray detecting elements which are arranged in at least one row transverse to the Y-axis and are at an opposite side of the patient position from the source;

supporting the source and detector on a source-detector support for movement as a unit relative to the patient position; and moving at least one of the patient table and the source-detector support relative to the other parallel to the Y-axis to scan the patient position with said fan beam in successive scans, said fan beam being at an angle relative to the patient position during at least one of said scans which is different than the angle during at least another one of said scans; and wherein the vertical distance between the origin of the fan beam and the patient table is the same as between said successive scans.

25. A method as in claim 24 in which said moving step comprises selectively moving the table parallel to the X-axis between said successive scans.

26. A method as in claim 25 in which said moving step comprises selectively moving the table parallel to the Z-axis between said successive scans.

27. A method as in claim 26 in which said moving step comprises selectively rotating the source-detector support between said successive scans about a rotation axis parallel to the Y-axis.

28. A method as in claim 24 in which said moving step comprises selectively moving the table parallel to each of the X-axis and the Z-axis between said successive scans and selectively rotating the source-detector support between said successive scans about a rotation axis parallel to the Y-axis and preventing movement of the source-detector support parallel to the X-axis.

29. A method as in claim 24 in which said moving step comprises causing the vertical from the origin of the fan beam to intersect the table at the same line parallel to the Y-axis during each of said successive scans.

30. A system as in claim 1 in which said scanning mechanism comprises a mechanism maintaining the vertical from the origin of the fan beam in a YZ plane which intercepts the table at the same place during each of said successive scans.

31. A method as in claim 15 in which said scanning step maintains the vertical from the origin of the fan beam in a YZ plane which intercepts the table at the same place during each of said successive scans.

32. A method as in claim 19 in which said moving step maintains the vertical from the origin of the fan beam in a YZ plane which intercepts the table at the same place during each of said successive scans.

* * * * *